United States Patent
Nakamura et al.

(10) Patent No.: US 7,181,792 B2
(45) Date of Patent: Feb. 27, 2007

(54) RADIOTHERAPEUTIC BED APPARATUS

(75) Inventors: Shin Nakamura, Hitachi (JP); Hiroshi Akiyama, Hitachiohta (JP); Junichi Yamashita, Hitachi (JP); Kyouichi Kawasaki, Sakura (JP); Yuuji Hosoda, Chiyoda (JP); Hiroyuki Sadamori, Chiyoda (JP); Hidehito Asano, Ogawa (JP); Yoshiyuki Nakamura, Hitachi (JP)

(73) Assignees: Hitachi, Ltd., Tokyo (JP); Hitachi Setsubi Engineering Co., Ltd., Tokyo (JP)

(*) Notice: Subject to any disclaimer, the term of this patent is extended or adjusted under 35 U.S.C. 154(b) by 14 days.

(21) Appl. No.: 10/911,787

(22) Filed: Aug. 5, 2004

(65) Prior Publication Data

US 2005/0028280 A1 Feb. 10, 2005

(30) Foreign Application Priority Data

Aug. 8, 2003 (JP) ............................. 2003-206659

(51) Int. Cl.
*A61G 13/00* (2006.01)

(52) U.S. Cl. ............................... 5/601; 5/608; 378/209
(58) Field of Classification Search .................... 5/601, 5/600, 607, 608, 610, 611, 11; 378/209, 378/208, 177, 179
See application file for complete search history.

(56) References Cited

U.S. PATENT DOCUMENTS

| | | | | |
|---|---|---|---|---|
| 3,240,935 A | * | 3/1966 | Dougall | 5/601 |
| 3,868,103 A | * | 2/1975 | Pageot et al. | 5/614 |
| 4,131,801 A | * | 12/1978 | Hogan | 5/601 |
| 4,156,815 A | * | 5/1979 | Hogan | 5/601 |
| 4,435,862 A | | 3/1984 | King et al. | |
| 4,761,000 A | * | 8/1988 | Fisher et al. | 5/608 |
| 5,013,018 A | * | 5/1991 | Sicek et al. | 5/601 |
| 5,014,292 A | * | 5/1991 | Siczek et al. | 378/196 |
| 5,398,356 A | * | 3/1995 | Pfleger | 5/608 |
| 6,094,760 A | * | 8/2000 | Nonaka et al. | 5/601 |
| 6,416,219 B1 | * | 7/2002 | Pflaum et al. | 378/209 |
| 6,637,056 B1 | | 10/2003 | Tybinkowski et al. | |
| 6,640,363 B1 | * | 11/2003 | Pattee et al. | 5/601 |
| 6,681,423 B2 | * | 1/2004 | Zachrisson | 5/610 |
| 6,977,985 B2 | * | 12/2005 | Bohn et al. | 378/27 |
| 7,099,432 B2 | * | 8/2006 | Ichihara et al. | 378/25 |
| 2002/0104464 A1 | | 8/2002 | Isensee et al. | |

(Continued)

FOREIGN PATENT DOCUMENTS

GB  743412  1/1956

(Continued)

*Primary Examiner*—Robert G. Santos
(74) *Attorney, Agent, or Firm*—Dickstein Shapiro LLP

(57) ABSTRACT

A therapeutic bed is arranged so that its inclination is adjusted by a bed inclination adjusting device provided to a rotation drive device disposed in a Y-direction moving device. The bed inclination adjusting device supports the therapeutic bed at three points by its three inclination adjusters. Each of the inclination adjusters converts the rotation of a motor into the rectilinear motion of a slider, and varies the level of a universal joint provided to the therapeutic bed by a support rod rotatably attached to the slider. This allows the inclination angle of the therapeutic bed to be varied. The provision of the bed inclination adjusting device reduces the number of drive devices for positioning the therapeutic bed, thereby decreasing the cumulative value of errors in all drive devices.

4 Claims, 8 Drawing Sheets

U.S. PATENT DOCUMENTS

2003/0145383 A1 8/2003 Schwaegerie
2005/0028280 A1* 2/2005 Nakamura et al. ............. 5/601

FOREIGN PATENT DOCUMENTS

| GB | 2 285 619 A | 7/1995 |
| JP | 1-151467 | 6/1989 |
| JP | 1-209077 | 8/1989 |
| JP | 02-09722 | 3/1990 |
| JP | 02-102255 | 8/1990 |
| JP | 07-051320 | 2/1995 |
| JP | 08-182711 | 7/1996 |
| JP | 09098969 | 4/1997 |
| JP | 11-47287 | 2/1999 |
| JP | 11-313900 | 11/1999 |
| JP | 11313900 | 11/1999 |
| WO | WO 02/32312 | 4/2002 |

* cited by examiner

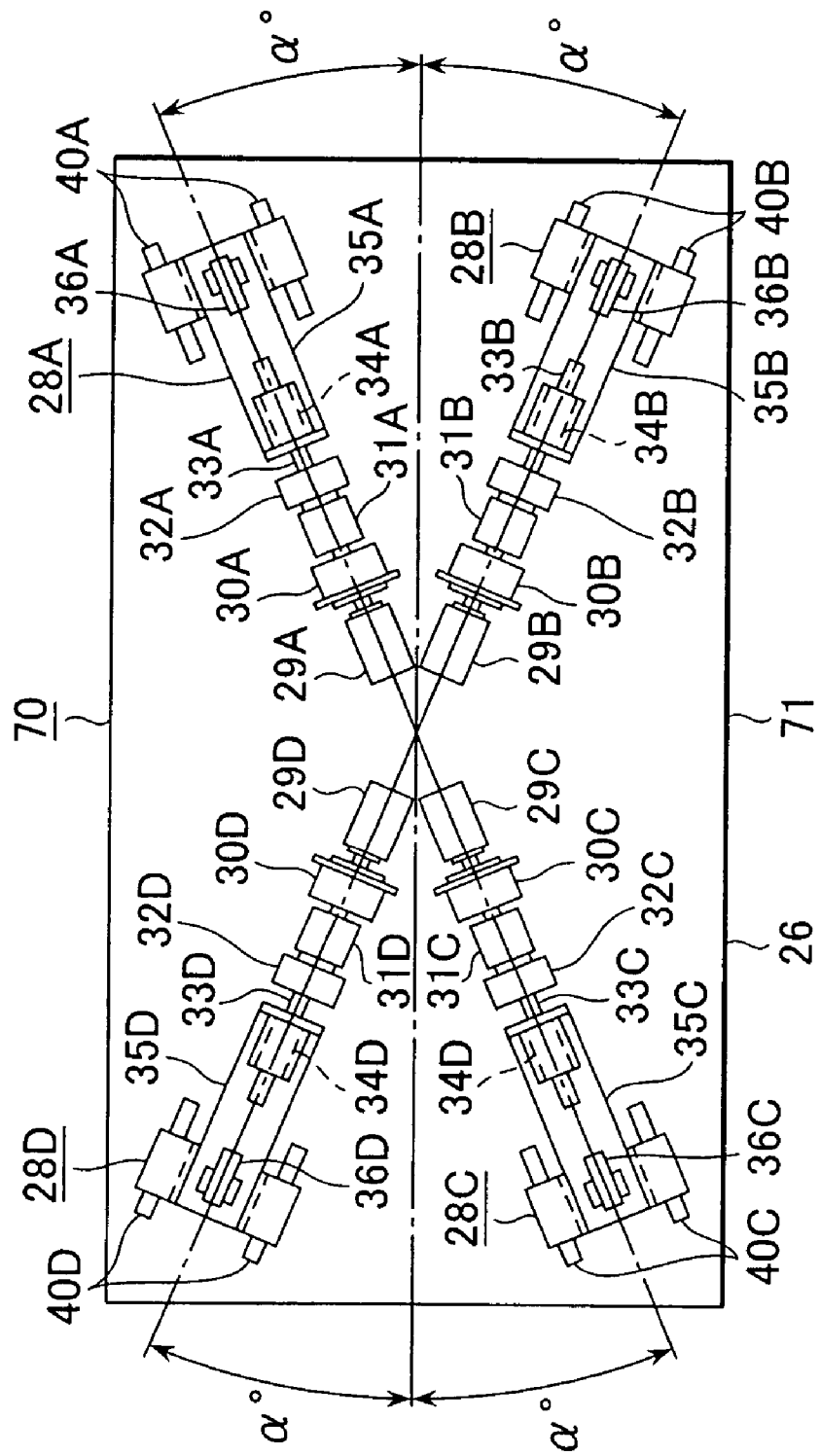

RADIOTHERAPEUTIC BED APPARATUS

BACKGROUND OF THE INVENTION

1. Field of the Invention

The present invention relates to a radiotherapeutic bed apparatus, and particularly to a radiotherapeutic bed apparatus suited to being incorporated into a particle beam therapeutic apparatus that irradiates the affected area of a patient with ion beams.

2. Description of the Related Art

In a radiotherapeutic bed apparatus, a bed on which a patient lies is inserted into a therapy room formed in a rotating gantry, and is aligned with an irradiation device (irradiation field forming device) provided in the rotating gantry. In this situation, the affected area of the patient lying on the bed is positioned on the extension line of the path of ion beams in the irradiation device. The particle beam therapeutic apparatus includes an accelerator and the irradiation device. Ion beams accelerated by the accelerator are applied from the irradiation device to the affected area of the patient lying on the bed.

As an example of a radiotherapeutic bed apparatus (hereinafter, simply referred to as a "bed apparatus"), a bed apparatus disclosed in JP, A 11-313900 is known. As shown in FIG. 2 in the above patent document, this bed apparatus includes a bed on which a patient to lie; an X-axis direction moving device for moving the bed in the X-axis direction; a Y-axis direction moving device for moving the bed in the Y-axis direction; a Z-axis direction moving device for moving the bed in the Z-axis direction; a rotation drive device for rotating the bed; a pitching drive device for driving the bed to pitch, and a rolling drive device for driving the bed to roll.

More specifically, in the bed apparatus shown in FIG. 2 in the JP, A 11-313900, the Z-axis direction moving device is disposed on the X-axis direction moving device, and the Y-axis direction moving device is disposed on the Z-axis direction moving device. A bed base to be rotated by the rotation drive device is disposed on the Y-axis direction moving device; a rotational base to be driven to roll by the rolling drive device is disposed on the bed base; and the therapeutic bed to be driven to pitch by the pitching drive device is disposed on the rotational base. Also, in another bed apparatus shown in FIGS. 12 and 13 in the JP, A 11-313900, a hinge base to be driven to pitch by a pitching drive device is disposed on a bed base, and a radiotherapy bed to be driven to roll by a rolling drive device is disposed on the hinge base.

SUMMARY OF THE INVENTION

Each bed apparatus set forth in the above-described JP, A 11-313900 has six drive devices arranged in series: the X-axis direction moving device, Z-axis direction moving device, Y-axis direction moving device, rotation drive device, rolling drive device, and pitching drive device, that is, six serial links. As a result, the positioning accuracy with respect to a therapeutic bed using such a conventional bed apparatus that has six degrees of freedom, is subjected to the influence of a positioning error with respect to each of the drive devices disposed in series. Here, the magnitude of a positioning error in the conventional bed apparatus is represented by the cumulative value of positioning errors in the six drive devices.

In a particle beam therapeutic device, for accurately performing the application of ion beams to the affected area of a patient, it is desirable to enhance the positioning accuracy of the bed apparatus with respect to the therapeutic bed on which the patient lies. This entails reduction in positioning error with respect to the bed apparatus.

Accordingly, it is an object of the present invention to provide a radiotherapeutic bed apparatus capable of enhancing the positioning accuracy with respect to a therapeutic bed.

To achieve the above-described object, the present invention provides a radiotherapeutic bed apparatus comprising an inclination adjusting device provided to a bed drive device for adjusting the inclination of a bed supporting a patient, wherein the inclination adjusting device includes a plurality of movable support members supporting the bed at a plurality of support points and adjusting the levels of the respective supporting points. Such an arrangement allows the number of the drive axes for adjusting the inclination of the bed to be reduced by one. Conventionally, the inclination of the bed has been adjusted by two drive axes: a drive axis of the pitching drive device and that of rolling drive device, whereas in the present invention, the inclination of the bed can be adjusted by a single drive axis of the inclination adjusting device. The present invention, therefore, allows the cumulative value of errors in all drive devices for positioning the bed to be reduced, thereby enhancing the positioning accuracy with respect to the bed.

BRIEF DESCRIPTION OF THE DRAWINGS

FIG. 10 is a constructional view of a bed inclination adjuster for a radiotherapeutic bed apparatus according to another embodiment of the present invention.

DESCRIPTION OF THE PREFERRED EMBODIMENTS

Figure 8:
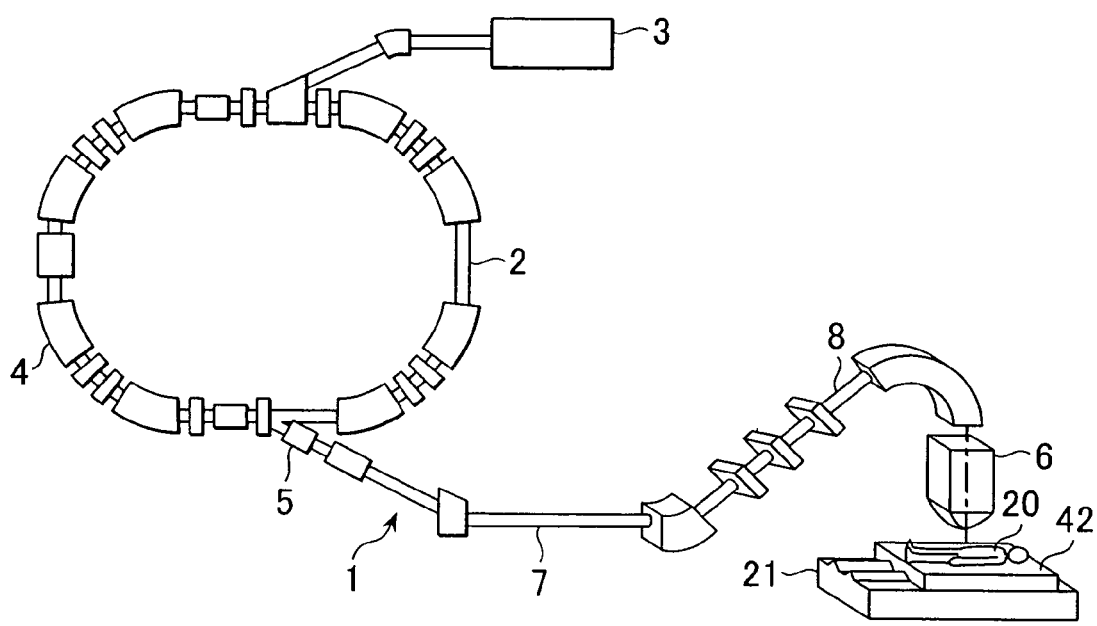
FIG. 8 is a schematic constructional view of a particle beam therapeutic apparatus into which the radiotherapeutic bed apparatus in FIG. 1 is incorporated.

A particle beam therapeutic apparatus into which the radiotherapeutic bed apparatus according to one preferred embodiment of the present invention is incorporated, will be described with reference to FIGS. 8 and 9. The particle beam therapeutic apparatus 1 includes a charged particle beam generating device 2, rotating gantry 9 (FIG. 9), charged particle beam irradiation device (particle ray irradiation device) 6, and radiotherapeutic bed apparatus 21. The charged particle beam generating device (particle ray generating device) 2 has an ion source (not shown), pre-stage accelerator 3, and synchrotron 4. Ions generated at the ion source, e.g., proton ions (or carbon ions) are accelerated by the pre-stage accelerator (e.g., linear accelerator) 3. The ion beams (e.g., proton beams) are applied from the pre-stage accelerator 3 to the synchrotron 4. In this embodiment, proton beams are used as the ion beams. The ion beams, which are charged particle beams (particle rays), are accelerated by the synchrotron 4, and after their energy has been enhanced up to a set energy, they are emitted from a deflector 5 for emission.

The ion beams emitted from the synchrotron 4 reach the charged particle beam irradiation device (irradiation field forming device) 6 serving as a particle beam irradiation section, through a beam transport system 7. Hereinafter, the charged particle beam irradiation device is simply referred to as an "irradiation device." The charged particle beam irradiation device 6, and an inverse U-shaped beam transport device 8, which is a portion of the beam transport system 7, are disposed in a rotating drum (FIG. 9) 10 of the rotating gantry 9, and they rotate as the rotating gantry 9 rotates. The ion beams are applied from the irradiation device 6 to the affected area (cancer-affected area) of a patient 20 lying on the therapeutic bed 42 through the beam transport device 8.

Figure 9:
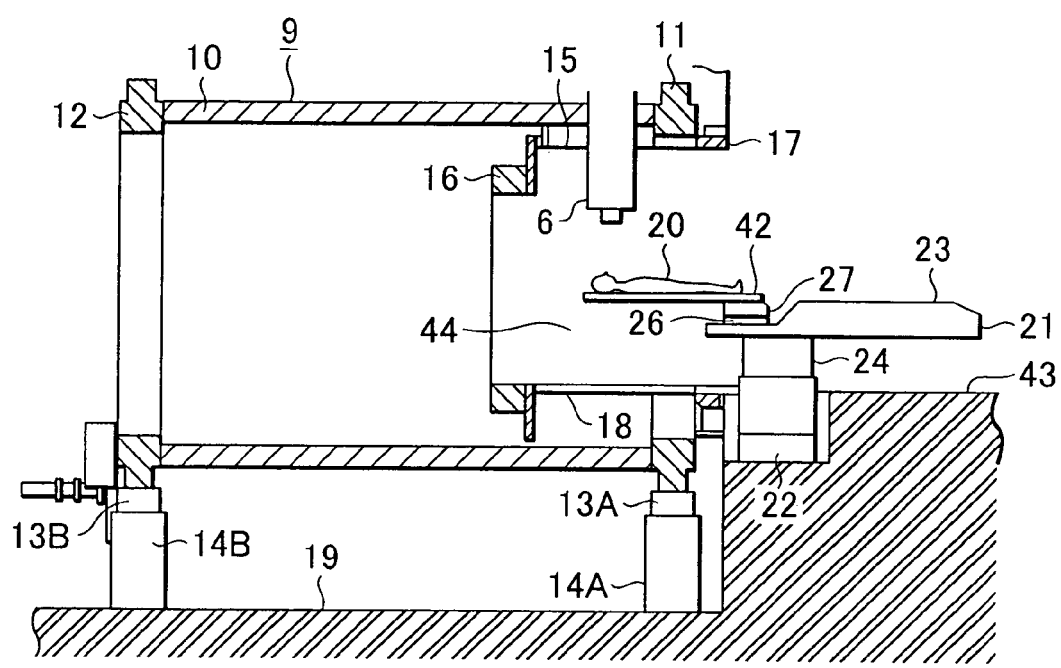
FIG. 9 is a representation explaining the radiotherapeutic bed apparatus inserted into a therapy room formed in a rotating gantry.

As shown in FIG. 9, the rotating gantry 9 has a cylindrical rotating drum (rotating body) 10 including a front ring 11 and rear ring 12. The front ring 11 provided at an end of the rotating drum 10 is supported by a plurality of rotatable support rolls 13A provided on a support unit 14A. The rear ring 12 provided at the other end of the rotating drum 10 is also supported by a plurality of support rolls 13B rotatably provided on a support unit 14B.

A particle beam therapeutic irradiation room 15 is disposed in the rotating drum 10. The particle beam therapeutic irradiation room 15 includes a rotatable annular frame 16, fixed annular frame 17, and movable floor 18. The annular frame 17 is disposed on the front ring 11 side, and is fixed to a stand (not shown) provided in a rotating gantry installation area 19. The annular frame 16 is disposed on the other end side of the rotating drum 6 with the movement path of the irradiation device 6 between the annular frames 16 and 17. The annular frame 16 is supported by a plurality of support rolls (not shown) rotatably mounted to a support frame (not shown) fixed to the inner side of the rotating drum 10. Each of the annular frames 16 and 17 has a ring guide section (not shown) on the respective one of the opposite side surfaces, the ring guide section having a guide groove that includes a horizontal portion formed at its lowest portion and an arcuate portion formed at its upper portion. The guide groove has a semicylindrical-shaped groove including the horizontal groove portion and arcuate groove portion that are connected to each other. As shown in FIGS. 1 to 5 in JP, A 11-47287, the movable floor is disposed so as to be movable in the guide groove.

Figure 1:
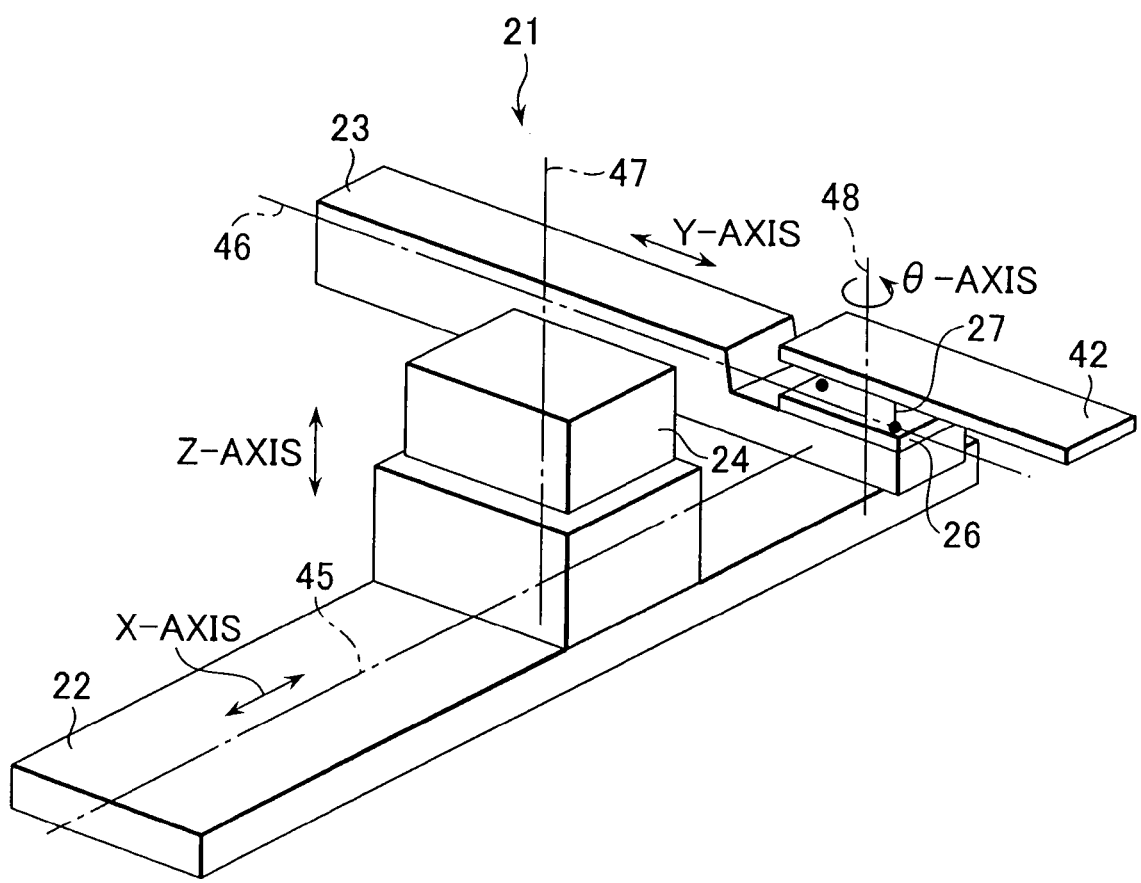
FIG. 1 is a perspective view of a radiotherapeutic bed apparatus according to a preferred embodiment of the present invention.
Figure 2:
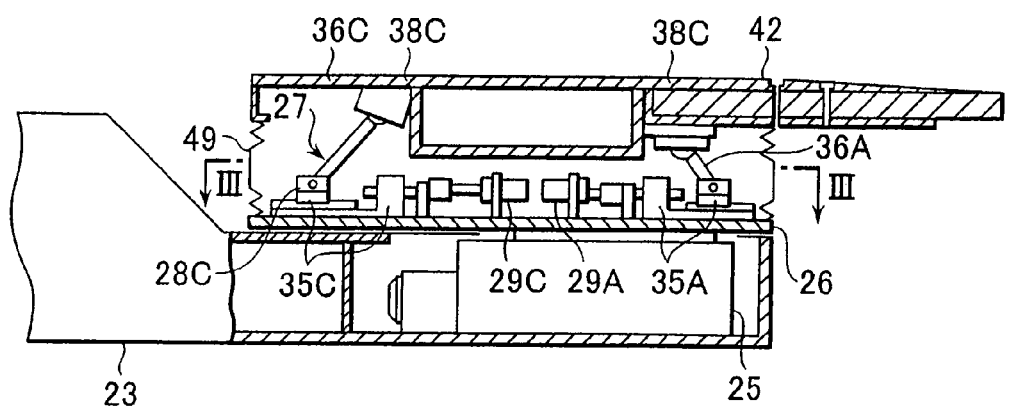
FIG. 2 is a longitudinal sectional view showing the vicinity of the bed base shown in FIG. 1.

The radiotherapeutic bed apparatus according to this embodiment, that is, the bed apparatus 21, will be described below with reference to FIGS. 1 and 2. The bed apparatus 21 comprises an X-direction moving device 22, Y-direction moving device 23, Z-direction moving device (up-and-down direction moving device) 24, rotation drive device 25, bed inclination adjusting device (parallel link device) 27, and therapeutic bed 42. The bed inclination adjusting device 27 is an inclination adjusting device for adjusting the inclination of the bed.

The X-direction moving device 22 is disposed in the bed apparatus installation area 43 located higher than the rotating gantry installation area 19 (see FIG. 9). The X-direction moving device 22 and Z-direction moving device 24 are disposed opposite to the front ring 11, outside the rotating gantry 10. The Z-direction moving device 24 is disposed on the X-direction moving device 22; the Y-direction moving device 23 is disposed on the Z-direction moving device 24; and the rotation drive device 25 is provided to the Y-direction moving device 23. The bed inclination adjusting device 27 is provided to the rotation drive device 25, and supports the therapeutic bed 42 (see FIG. 2). The therapeutic bed 42 is moved by the X-direction moving device 22 in the direction of a joint axis 45 (X-axis) parallel to the plane of the front ring 11 and extending in the horizontal direction. As shown in FIG. 1, the therapeutic bed 42 is moved by the Z-direction moving device 24 in the direction of a joint axis 47 (Z-axis) perpendicular to the joint axis 45. Also, the therapeutic bed 42 is moved by the Y-direction moving device 23 in the direction of a joint axis 46 (Y-axis) that is perpendicular to each of the joint axis 45 (X-axis) and joint axis 47 (Z-axis) and that extends in the direction of the rotational axis of the rotating drum 10. Namely, the therapeutic bed 42 is inserted into and retracted from the therapy room 44 by the Y-direction moving device 23. Moreover, the therapeutic bed 42 is rotated by the rotation drive device 25 about a joint axis 48 (θ-axis) perpendicular to the joint axis 46 (Y-axis). The therapy room 44 is surrounded by the movable floor 18 in the rotating gantry 9.

Figure 3:
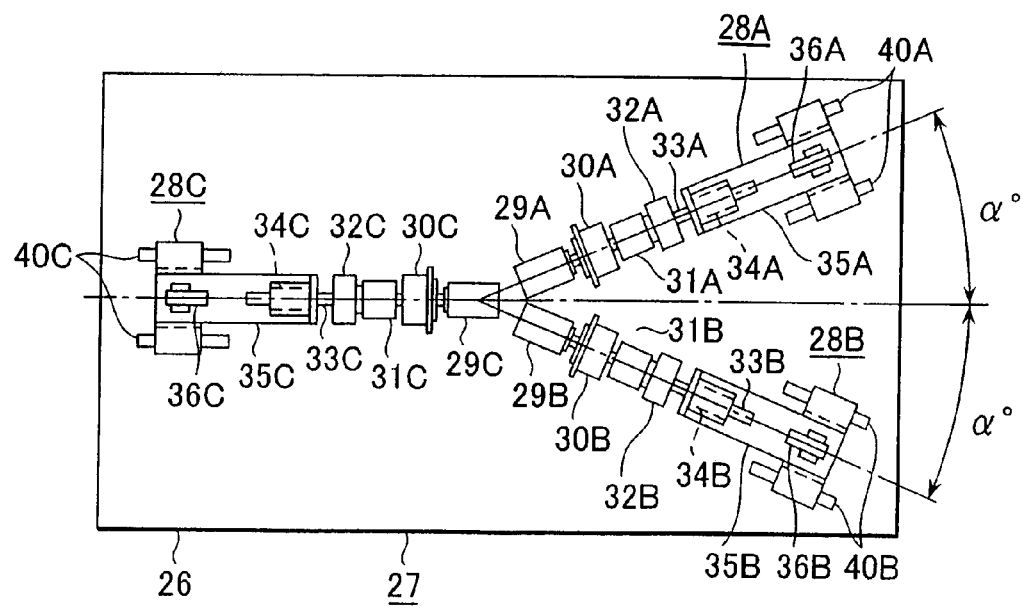
FIG. 3 is a longitudinal sectional plan view taken along the line III—III line in FIG. 2.

As shown in FIG. 3, the bed inclination adjusting device 27 includes a base 26, and three inclination adjusters (movable support members) 28A, 28B, and 28C. The base 26 is provided to the rotation drive device 25. The top surface of the base 26 is a plan perpendicular to the moving direction of the Z-direction moving device 24, i.e., up-and-down direction moving device. The three inclination adjusters 28A, 28B, and 28C are disposed on the base 26. The therapeutic bed 42 is supported at three points by the bed inclination adjusting device 27, i.e., the three inclination adjusters 28A, 28B, and 28C,. in a state of being inclined in an arbitrary direction. The inclination adjusters 28A, 28B, and 28C have the same construction. However, the inclination adjuster 28C is larger than the inclination adjusters 28A and 28B. The inclination adjuster 28C is disposed on the base 26 along the Y-axis. The inclination adjusters 28A and 28B are symmetrically disposed with respect to the Y-axis, and each arranged so as to form a predetermined angle (αdegrees) with respect to the Y-axis in the horizontal direction on the base 26. A bellows-type cover 49 is attached to the base 26 and the therapeutic bed 42 so as to enclose the bed inclination adjusting device 27.

Figure 4:
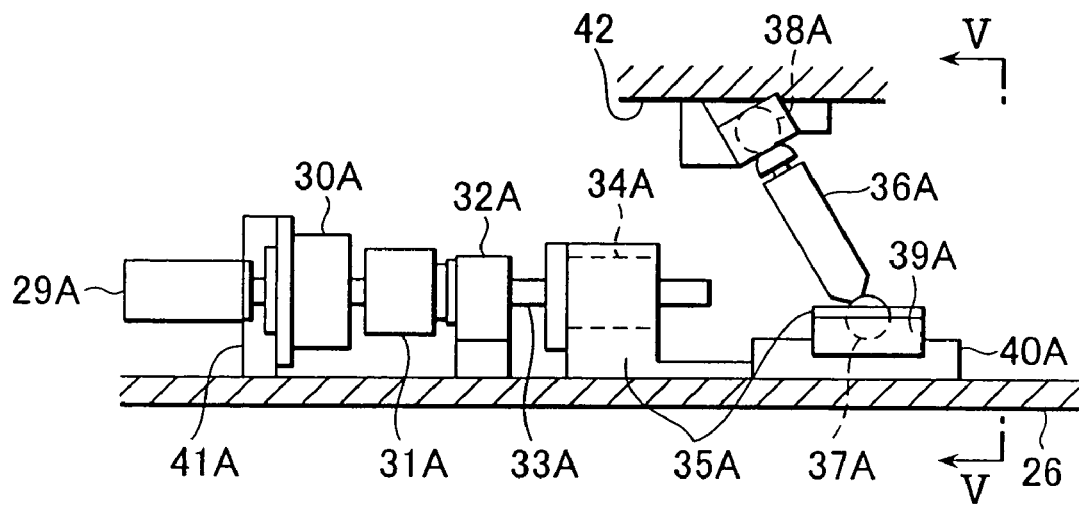
FIG. 4 is a side view of the inclination adjuster shown in FIG. 2.
Figure 5:
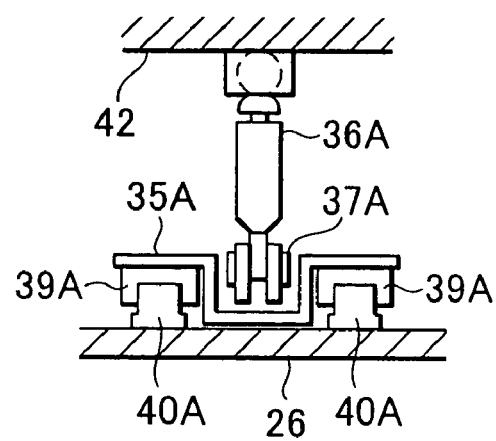
FIG. 5 is a cross-sectional plan view taken along the line V—V line in FIG. 4.

Next, the construction of the inclination adjusters will be described taking the inclination adjuster 28A as an example. As shown in FIGS. 4 and 5, the inclination adjuster 28A includes a servomotor 29A, ball screw 33A, nut 34A, slider 35A, and support rod 36A. The servomotor 29A is attached to a support member 41A provided on the base 26, and coupled to the ball screw 33A through a decelerator 30A and coupling 31A. The ball screw 33A is supported by the base 26 through a bearing 32A, and engaged with the nut 34A provided to the slider 35A. The slider 35A is attached to a pair of linear guides 39A each slidably engaged with a respective one of a pair of linear guides 40A provided on the base 26. The support rod 36A is attached to the slider 35A so as to be rotatably by a pin joint 37A. The other end of the support rod 36A remote from the slider 35A has a spherical shape, and is engaged with a universal joint 38A disposed on the undersurface of the therapeutic bed 42. The position where the universal joint 38A is attached in the therapeutic bed 42 constitutes the support point of the inclination adjuster 28A. In all components of the inclination adjusters 28B and 28C, and those of the inclination adjusters 28A, components designated by the same numeral parts of the reference characters have the same functions. The therapeutic bed 42 is supported by the support rods 36A, 36B, and 36C of the inclination adjusters 28A, 28B, and 28C disposed on the base 26.

Figure 7:
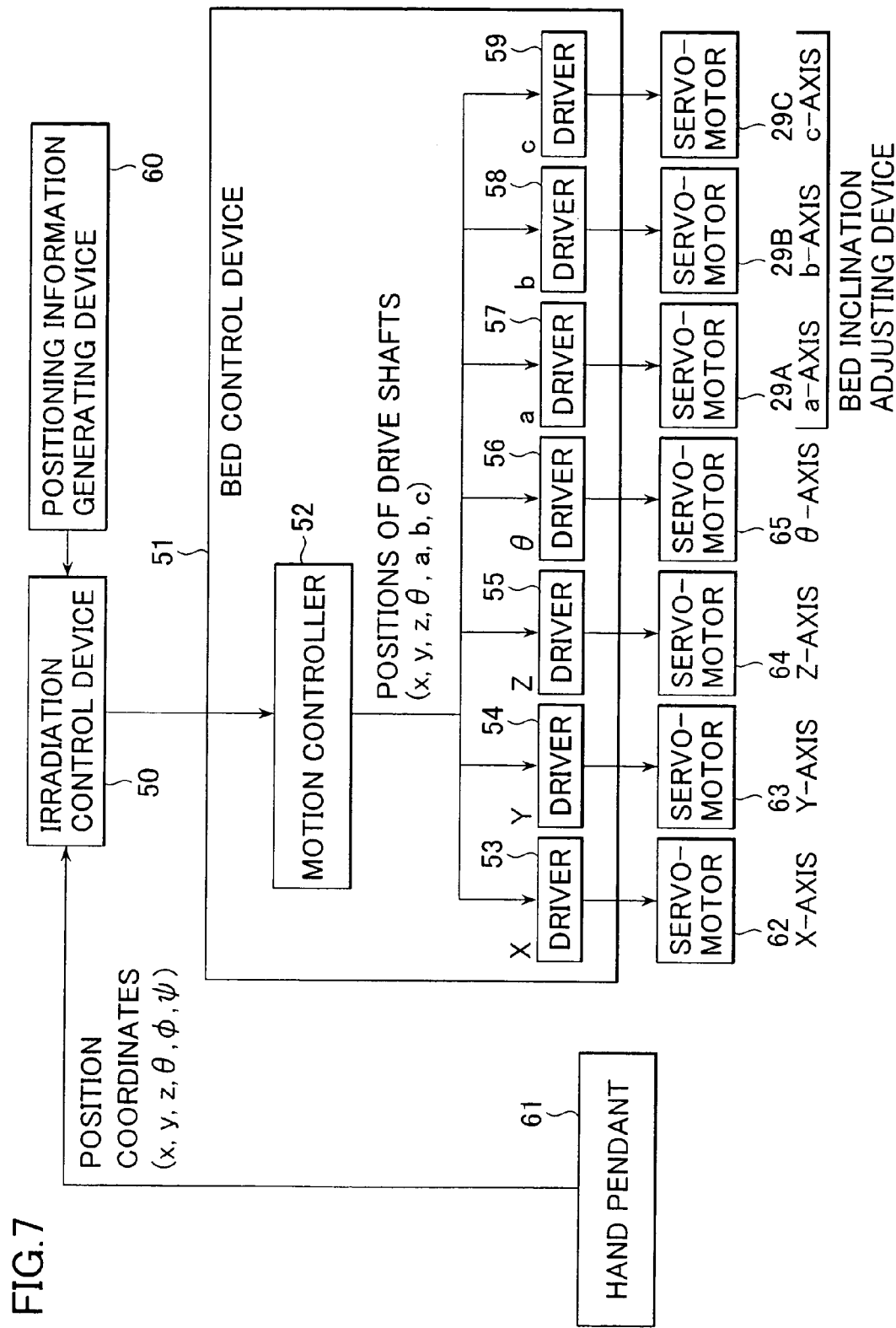
FIG. 7 is a block diagram of a control system for controlling the radiotherapeutic bed apparatus shown in FIG. 1.

Here, a control system that performs positioning of the therapeutic bed 42 in the bed apparatus 21 will be described. As shown in FIG. 7, this control system includes an irradiation control device 50, bed control device 51, positioning information generating device 60, and hand pendant 61. The hand pendant 61 is disposed in the therapy room 44, and is operated by a radiological technician having entered the therapy room 44 when he/she performs coarse positioning of the therapeutic bed 42. The hand pendant 61 is connected to the irradiation control device 50. The positioning information generating device 60 is also connected to the irradiation control device 50. The irradiation control device 50 is connected to the bed control device 51. The bed control device 51 comprises a motion controller 52 and drivers 53 to 59.

In the bed apparatus 21 according to this embodiment, before being irradiated with ion beams, the affected area of a patient 20 lying on the therapeutic bed 42 must be positioned in the beam path of the irradiation device 6. For this purpose, firstly, control by a gantry control device (not shown) is performed by using angular information on the rotating gantry 9 (i.e., information on irradiation direction of ion beams), which constitutes one piece of treatment plan information. This control allows the rotating gantry 9 to be rotated and enables the beam path in the irradiation device 6 to be moved to the angle corresponding to the aforementioned angular information. Thereafter, the therapeutic bed 42 on which the patient lies is moved to a predetermined position in the therapy room 44, that is, moved so that the affected area of the patient 20 is aligned with the beam path of the irradiation device 6. The movement of the therapeutic bed 42 is controlled by the bed control device 51. Specifically, an operator, such as a radiological technician, present in the therapy room 44 inputs a therapeutic bed movement command to the irradiation control device 50 using an input device for the hand pendant 61. This movement command includes position coordinates (x, y, z) in the X-axis direction, Y-axis direction, and Z-axis direction; a rotation angle $\theta$ about the $\theta$-axis; a pitching angle $\phi$; and a rolling angle $\psi$. The irradiation control device 50 outputs the therapeutic bed movement command inputted, to the motion controller 52 of the bed control device 51. Based on the therapeutic bed movement command inputted, the motion controller 52 calculates moved positions (X, Y, Z, $\Theta$, a, b, c) of the X-direction moving device 22, Y-direction moving device 23, Z-direction moving device 24, rotation drive device 25, and inclination adjusters 28A, 28B, and 28C. That is, the calculation of the moved positions (X, Y, Z, $\Theta$, a, b, c) is performed by coordinate conversions using the values (x, y, z, $\theta$, $\phi$, $\psi$) of the therapeutic bed movement command. As shown in FIG. 7, the motion controller 52 outputs the calculated values (X, Y, Z, $\Theta$, a, b, c) to the respective pertinent drivers 53 to 59. Here, "a", "b", and "c" each indicate the position of a pin joint in a moving direction of the slider of a respective one of the inclination adjusters 28A, 28B, and 28C.

The driver 53 drives a servomotor 62 for the X-direction moving device 22 to move the X-direction moving device 22, thereby positioning the therapeutic bed 42 at an X-position in the X-axis direction. The driver 54 drives a servomotor 63 for the Y-direction moving device 23 to move the Y-direction moving device 23, thereby positioning the therapeutic bed 42 at a Y-position in the Y-axis direction. The driver 55 drives a servomotor 64 for the Z-direction moving device 24 to move the Z-direction moving device 24, thereby positioning the therapeutic bed 42 at a Z-position in the Z-axis direction. The driver 56 drives a servomotor 65 for the rotation drive device 25 to rotate the rotation drive device 25 (together with the base 26), thereby positioning the therapeutic bed 42 at an angle $\Theta$ about the $\theta$-axis, which is an vertical axis. The driver 57 drives the servomotor 29A for the inclination adjusters 28A to move the slider 35A, thereby positioning the pin joint 37A at a position "a" in the axial direction of the ball screw 33A. The driver 58 drives a servomotor 29B for the inclination adjusters 28B to move a slider 35B, thereby positioning a pin joint 37B at a position "b" in the axial direction of a ball screw 33B. The driver 59 drives a servomotor 29C for the inclination adjusters 28C to move a slider 35C, thereby positioning a pin joint 37C at a position "c" in the axial direction of a ball screw 33C. In this manner, positioning the pin joints 37A, 37B, and 37C, respectively, at the position "a", "b", and "c" allows the therapeutic bed 42 to be inclined at a predetermined angle with respect to a horizontal plane.

The above-described control enables the therapeutic bed 42, and more specifically, the affected area of the patient 20 lying on the bed 42 to be positioned with respect to the beam path of the irradiation device 6.

Next, taking the inclination adjuster 28A as an example, inclining operations with respect to the therapeutic bed 42 by the inclination adjusters 28A, 28B, and 28C will be specifically described with reference to FIG. 6. The rotational force of the servomotor 29A is decelerated by the decelerator 30A and transmitted to the ball screw 33A through the coupling 31A. A pair of linear guides 39A provided to the slider 35A are each slidably engaged with a respective one of a pair of linear guides 40A disposed on the base 26, so that the rotation of the ball screw 33A is converted into a linear motion (linear motion in the axial direction of the ball screw 33A) of the slider (rectilinearly moving member) 35A by the nut 34A. This linear motion of the slider 35A allows the pin joint 37A to be positioned at the position "a", as described above.

Figure 6:
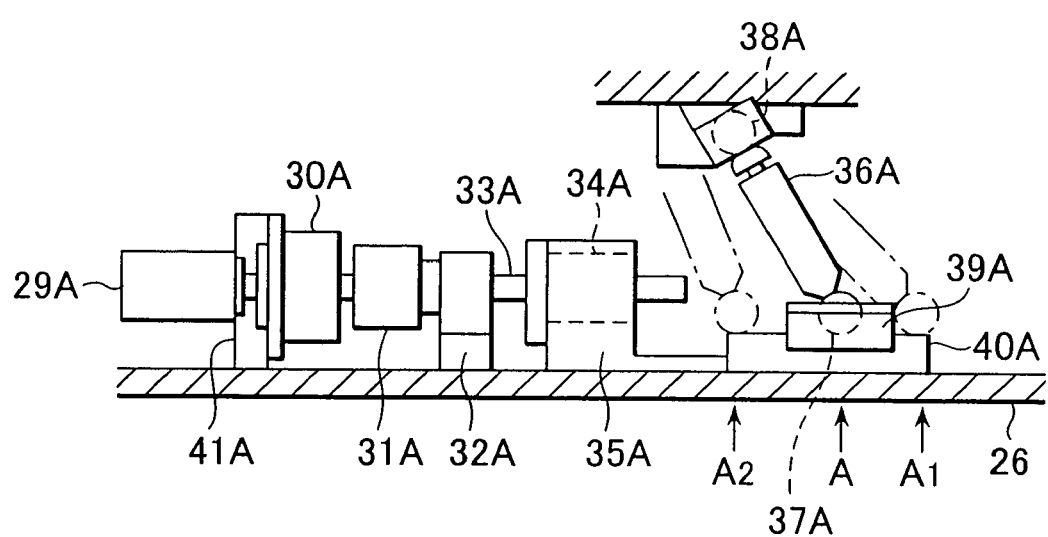
FIG. 6 is a representation explaining operations of the inclination adjuster shown in FIG. 2.

For example, as shown in FIG. 6, when the pin joint 37A located at the position A moves to a position $A_1$, the support rod 36A rotates about the pin joint 37A so that the inclination angle of the support rod 36A becomes smaller than its inclination angle at the position A. Since the other end of the support rod 36A is engaged with the universal joint 38A, the rotation of the support rod 36A moves the universal joint 38A downward. As a result, the portion of the therapeutic bed 42 where the universal joint 38A is attached, moves downward. Given that the therapeutic bed 42 is in a horizontal state when the pin joint 37A is located at the position A, the movement of the pin joint 37A to the position $A_1$ causes the therapeutic bed 42 to incline so that the universal joint side thereof is located downward.

Also, when the pin joint 37A located at the position A moves to a position $A_2$, the support rod 36A rotates about the pin joint 37A so that the inclination angle of the support rod 36A becomes larger than its inclination angle at the position A. The pin joint 37A constitutes the center of rotation of the support rod 36A on the slider 35A. The rotation of the support rod 36A moves the universal joint 38A upward. As a result, the portion of the therapeutic bed 42 where the universal joint 38A is attached, moves upward. The therapeutic bed 42, which is in a horizontal state when the pin joint 37A is located at the position A, inclines so that the universal joint side thereof is located upward by the movement of the pin joint 37A to the position $A_2$.

Movement of the slider 35B of the inclination adjuster 28B allows the position in the height direction of a universal joint (not shown) engaged with the support rod 36B to be changed as described in the foregoing. This makes it possible to incline the therapeutic 42 in directions different from those in the case where the slider 35A is moved. Furthermore, movement of the slider 35C of the inclination adjuster 28C allows the position of the universal joint 38C in the height direction to be changed as described in the foregoing. This makes it possible to incline the therapeutic 42 in directions different from those in the case where the slider 35A is moved. By the above-described operations, the position of each of the universal joints in the height direction can be adjusted for the respective one of the inclination adjusters 28A, 28B, and 28C. This position adjustment enables the therapeutic bed 42 to be inclined in an arbitrary direction.

Conversely, the bed inclination adjusting device 27 can cause the therapeutic bed 42 that has been inclined to become horizontal by operating pertinent inclination adjusters. Also, when the therapeutic bed 42 on which a patient 20 lies is deflected in the longitudinal direction by the self weight of the patient 20 to thereby position its affected area below the isocenter, the deflection of the therapeutic bed 42 is corrected by lifting the head side of the patient 20 on the therapeutic bed 42 by operations of the inclination adjusters 28A and 28B. Specifically, the sliders 35A and 35B, respectively, are moved toward the motor side to rotate the support rods 36A and 36B in the direction so that they are raised, thereby lifting the head side of the patient 20 in the therapeutic bed 42. This allows the affected area to be aligned with the isocenter.

For example, when attempting to cause the therapeutic bed 42 to pitch, the sliders 35A and 35B of the inclination adjusters 28A and 28B are moved so as to go away from the respective servomotors while the slider 35C of the inclination adjuster 28C is moved so as to get near the servomotor. As necessary, the sliders 35A and 35B are moved so as to get near the respective servomotors while the slider 35C is moved so as to go away from the servomotor. Also, for example, when attempting to cause the therapeutic bed 42 to roll, the slider 35A is moved so as to go away from the servomotor while the slider 35B is moved so as to get near the servomotor, without moving the sliders 35C of the inclination adjuster 28C. In some case, the slider 35A is moved so as to get near the servomotor while the slider 35B is moved so as to go away from the servomotor.

Next, high-accuracy positioning using image information is performed with respect to the therapeutic bed 42. This positioning is performed by a method set forth in, for example, JP, A 1-151467. Specifically, X-rays from a first X-ray tube (not shown) having moved to the beam path in the irradiation device 6 are applied to the affected area of a patient 20 on the therapeutic bed 42 (first X-ray photographing). The X-rays having passed through the patient 20 are photographed by a first X-ray transparent image photographing device (not shown) disposed at a position opposed to the beam path with the patient 20 on the therapeutic bed 42 therebetween (the above first X-ray transparent image photographing device includes an image intensifier and television camera that are set forth in, for example, the JP, A 1-151467). The first X-ray transparent image photographing device outputs the first X-ray image information (first current image information) obtained by the photographing to the positioning information generating device 60 shown in FIG. 7. In addition, in the direction perpendicular to the beam path, X-rays from a second X-ray tube (not shown) are applied to the patient 20 (second X-ray photographing). The X-rays having passed through the patient 20 are photographed by a second X-ray transparent image photographing device (not shown) disposed at a position opposed to the beam path with the patient 20 therebetween (the above second X-ray transparent image photographing device has the same construction as that of the first X-ray transparent image photographing device). The second X-ray transparent image photographing device outputs the second X-ray image information (second current image information) obtained by the photographing to the positioning information generating device 60.

The positioning information generating device 60 generates positioning information with respect to therapeutic bed 42 using tomographic image information (basic image information) obtained by a preliminary X-ray CT (not shown) with respect to the patient, and the first and second current image information. The first and second current image information each corresponds to the "X-TV image" set forth in JP, A 1-209077, and first and second reference image information described later each correspond to the "reference image" set forth in the JP, A 1-209077.

First, the generation of positioning information using the first current image will be explained. Using the tomographic image information obtained by X-ray CT in advance, the positioning information generating device 60 generates tomographic image information (first reference image information, or first basic image information) viewed from the irradiation direction of X-rays at the first X-ray photographing. Using the first reference image information and first current image information, the positioning information generating device 60 calculates respective movement amounts of the therapeutic bed 42 in the X-axis direction and Y-axis direction, i.e., bed positioning information on the X-Y plane, and the rotation angle of the therapeutic bed 42, employing the equations ① to ● set forth in the JP, A 1-209077 (see FIGS. 3 and 4 in the JP, A 1-209077).

Next, the generation of positioning information using the second current image will be described. The positioning information generating device 60 generates tomographic image information (second reference image information, or second basic image information) viewed from the irradiation direction of X-rays at the second X-ray photographing. Using the second reference image information and second current image information, the positioning information generating device 60 calculates a movement amount of the therapeutic bed 42 in the Z-axis direction, i.e., bed positioning information on the Z-X plane, employing the concepts of the equations ① to +set forth in the JP, A 1-209077 (see FIG. 5 in the JP, 1-209077).

The bed control device 51 controls servomotors 62 to 65 based on the respective calculated movement amounts of the therapeutic bed 42 in the X-axis direction, Y-axis direction, and Z-axis direction, and the calculated rotation angle of the therapeutic bed 42 each of which has been inputted from the positioning information generating device 60. Specifically, the motion controller 52 calculates new position information $(X_1, Y_1, Z_1, \Theta_1)$ in the X-, Y-, and Z-axis directions, and about θ-axis, based on the position information $(X, Y, Z, \Theta)$ on the therapeutic bed 42 positioned by the operation of the hand pendant 61, and the above-described respective movement amounts calculated and calculated rotation angle. The driver 53 drives the servomotor 62 to position the therapeutic bed 42 at an $X_1$ position; the driver 54 drives the servomotor 63 to position the therapeutic bed 42 at a $Y_1$ position; the driver 55 drives the servomotor 64 to position the therapeutic bed 42 at a $Z_1$ position; and the driver 56 drives the servomotor 65 to position the therapeutic bed 42 at an angle of $\Theta_1$. Such a control by the bed control device 51 allows the therapeutic bed 42 to be positioned so that the affected area of the patient 20 aligns with the beam path of the irradiation device 6 and the rotational axis (isocenter) of the rotating drum 10.

In each of the inclination adjusters 28A, 28B, and 28C, the motor for moving a respective one of the sliders may be changed to a drive device including a cylinder and a piston provided in the cylinder. Specifically, a cylinder may be provided on the base 26, and a piston inserted in the cylinder may be connected to the slider using a piston rod. By supplying compressed air into the cylinder, the slider can be moved along the top surface of the base 26.

The bed apparatus according to this embodiment includes five drive devices: the X-direction moving device 22, Z-direction moving device 24 on the X-direction moving device 22, Y-direction moving device 23 on the Z-direction moving device 24, rotation drive device 25 on the Y-direction moving device 23, and bed inclination adjusting device 27 (comprising inclination adjusters 28A, 28B, and 28C) on the base 26 provided on the rotation drive device 25, that is, five serial links. The bed apparatus according to this embodiment has serial links that are one less than the conventional bed apparatus set forth in the above-described JP, A 11-313900, which has six drive devices: the X-axis direction moving device, Z-axis direction moving device, Y-axis direction moving device, rotation drive device, rolling drive device, and pitching drive device, that is, six serial links. As a consequence, in the bed apparatus 21, the cumulative value of errors in the drive devices for positioning the therapeutic bed 42 becomes smaller than that in the conventional bed apparatus. In other words, the bed apparatus 21 ensures superior positioning accuracy with respect to the therapeutic bed 42 as compared to the conventional bed apparatus. This is because the value of positioning error in the bed inclination adjusting device 27 according to this embodiment is smaller than the accumulation value of positioning errors in the rolling drive device and the pitching drive device of the conventional bed apparatus. Here, the value of positioning error in the bed inclination adjusting device is represented by an average value of positioning error values of the three inclination adjusters parallel disposed on the base 26 for supporting the therapeutic bed 42.

The bed apparatus according to this embodiment can support the therapeutic bed 42 by the bed inclination adjusting device 27 for adjusting the inclination angle of the therapeutic bed 42. This eliminates the need to specially provide support devices for the therapeutic bed 42 (for example, the rotating base 74 and supporting member 75 shown in FIG. 2 in the JP, A 11-313900), thereby simplifying the construction of the therapeutic bed 42. Since the therapeutic bed 42 is supported by the three support rods 36A, 36B, and 36C of the bed inclination adjusting device 27, it can be stably held to the rotation drive device 25 even in a state where the patient lies thereon.

Also, in this embodiment, since the bed inclination adjusting device 27 has the three inclination adjusters disposed on the base 26, the inclination of the therapeutic bed 42 can be adjusted in an arbitrary direction. This allows the affected area of the patient 20 lying on the therapeutic bed 42 to be easily positioned on the extension line of the beam path in the irradiation device 6, in the irradiation direction of ion beams determined by a treatment planning. Moreover, in this embodiment, each of the inclination adjusters includes a rectilinearly moving member (slider), which moves along a plane perpendicular to the moving direction of the Z-direction moving device 24, and a support rod rotatably attached to the rectilinearly moving member and supporting the therapeutic bed 42. Therefore, the height of the Z-direction moving device 24 in the moving direction can be maintained lower than the case where the rectilinearly moving member is arranged to move in the moving direction of the Z-direction moving device 24. This enables the distance between the therapeutic bed 42 and the rotation drive device 25 to be smaller, thereby reducing the size of the bed apparatus 21.

In this embodiment, the maintenance of the bed inclination adjusting device 27, i.e., the inclination adjusters 28A, 28B, and 28C can be performed by merely detaching a cover 49, without the need to remove the therapeutic bed 42. Thus, the bed apparatus according to this embodiment facilitates the maintenance of the bed inclination adjusting device 27. In contrast, in the bed apparatus shown in FIG. 2 in the JP. A 11-313900, the pitching drive device and rolling drive device cannot be subjected to maintenance unless the therapeutic bed is removed.

Another embodiment of a radiotherapeutic bed apparatus according to the present invention will be now described. The radiotherapeutic bed apparatus 70 according to this embodiment is different from the radiotherapeutic bed apparatus 21 shown in FIG. 1 only in the construction of a bed inclination adjusting device. Here, the bed inclination adjusting device 71 (parallel link device) in the radiotherapeutic bed apparatus 70 is explained with reference to FIG. 10. The bed inclination adjusting device 71 is disposed on the base 26 and supports the therapeutic bed 42, as well. The bed inclination adjusting device 71 includes inclination adjusters 28A, 28B, 28C, and 28D disposed on the base 26. Namely, the bed inclination adjusting device 71 has an arrangement in which one more inclination adjusters 28D is added to the bed inclination adjusting device 27. In this embodiment, the inclination adjusters 28C and 28D are also symmetrically disposed with respect to the Y-axis, and each arranged so as to form a predetermined angle ($\alpha$ degrees) with respect to the Y-axis in the horizontal direction on the base 26. The inclination adjusters 28D has the same construction as that of the inclination adjusters 28C. That is, the inclination adjuster 28D includes a servomotor 29D, ball screw 33D, nut 34D, slider 35D, and support rod 36D. The servomotor 29D attached to a support member (not shown) provided on the base 26, is coupled to the ball screw 33D through a decelerator 30D and coupling 31D. The ball screw 33D is supported by the base 26 through a bearing 32D, and engaged with the nut 34D provided to the slider 35D. The slider 35D is attached to a pair of linear guides (not shown) each slidably engaged with a respective one of a pair of linear guides 40D provided on the base 26. The support rod 36D is attached to the slider 35D so as to be rotatably by a pin joint (not shown). The other end of the support rod 36D remote from the slider 35D has a spherical shape, and is engaged with a universal joint (not shown) disposed on the undersurface of the therapeutic bed 42.

The radiotherapeutic bed apparatus 70 according to this embodiment can obtain the effect produced by the radiotherapeutic bed apparatus 21. Furthermore, the bed apparatus 70 according to this embodiment, supporting the therapeutic bed 42 by four support rods, can support the therapeutic bed 42 on which the patient lies more stably than the radiotherapeutic bed apparatus 21. However, since the bed apparatus 70 according to this embodiment has one more support rod, control programs of coordinate conversions and the like in the bed control device 51 become complicated correspondingly, as compared with the control programs in the bed control device 51 of the radiotherapeutic bed apparatus 21.

In the radiotherapeutic bed apparatuses 21 and 70 according to the above-described embodiments, the rectilinearly moving member of each of the inclination adjusters is arranged to move along a plane perpendicular to the moving direction of the Z-direction moving device. However, the rectilinearly moving member to be moved by the servomotor may be arranged to move in the moving direction of the Z-direction moving device 24, with the therapeutic bed 42 supported by a support rod rotatably attached to the rectilinearly moving member.

According to the present invention, since the number of serial links becomes one less than the conventional art, use of the present invention enables superior positioning accuracy with respect to the therapeutic bed as compared to the conventional art.

What is claimed is:

1. A radiotherapeutic bed apparatus comprising:
   a bed for supporting a patient;
   a bed drive device for moving said bed for positioning an affected area of the patient in an irradiation position of radiation emitted from an irradiation section; and
   an inclination adjusting device provided to said bed drive device for adjusting the inclination of the bed,
   wherein the inclination adjusting device including a plurality of movable support members supporting said bed at a plurality of support points and adjusting the levels of the respective supporting points,
   wherein each of said movable support members comprises a support rod attached to a corresponding one of the plurality of support points, and a support rod drive device for moving said support rod and adjusting the level of the support point at which the support rod is attached,
   wherein each support rod is rotatably attached to the corresponding one of said support points and said support rod drive device, and
   wherein each support rod drive device comprises a rectilinearly moving member to which said support rod is rotatably attached, and a drive device for moving the rectilinearly moving member in a direction perpendicular to the vertical direction.

2. The radiotherapeutic bed apparatus according to claim 1, wherein the inclination adjusting device has at least three of the support rods.

3. The radiotherapeutic bed apparatus according to claim 1, wherein:
   said bed drive device comprises:
      a bed moving device for independently moving said bed in respective directions of three axes that intersect orthogonally with one another, and
      a rotation drive device provided to said bed moving device for rotating the bed about a vertical axis; and
   wherein said inclination adjusting device is provided to said rotation drive device.

4. The radiotherapeutic bed apparatus according to claim 3, wherein said bed moving device comprises:
   an X-axis direction moving device for moving the bed in an X-axis direction;
   a vertical direction moving device provided to said X-axis direction moving device for moving the bed in a vertical direction perpendicular to said X-axis direction; and
   a Y-axis direction moving device provided to said vertical direction moving device for moving the bed in a Y-axis direction orthogonally intersecting each of said X-axis direction and said vertical direction.

* * * * *